(12) United States Patent
Wirtz et al.

(10) Patent No.: US 11,278,741 B2
(45) Date of Patent: Mar. 22, 2022

(54) MAGNETIC RESONANCE ANTENNA WITH ELECTRONIC DOSIMETERS

(71) Applicant: KONINKLIJKE PHILIPS N.V., Eindhoven (NL)

(72) Inventors: Daniel Wirtz, Eindhoven (NL); Christoph Leussler, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1317 days.

(21) Appl. No.: 15/124,742

(22) PCT Filed: Mar. 5, 2015

(86) PCT No.: PCT/EP2015/054598
§ 371 (c)(1),
(2) Date: Sep. 9, 2016

(87) PCT Pub. No.: WO2015/135825
PCT Pub. Date: Sep. 17, 2015

(65) Prior Publication Data
US 2017/0014643 A1    Jan. 19, 2017

(30) Foreign Application Priority Data

Mar. 13, 2014 (EP) .................... 14159359

(51) Int. Cl.
*A61N 5/10* (2006.01)
*G01R 33/34* (2006.01)
(Continued)

(52) U.S. Cl.
CPC ............ *A61N 5/1049* (2013.01); *A61B 5/055* (2013.01); *A61N 5/1071* (2013.01);
(Continued)

(58) Field of Classification Search
CPC .... A61N 2005/0627; A61N 2005/0628; A61N 5/1071; A61N 5/1075; A61N 2005/1055
See application file for complete search history.

(56) References Cited

U.S. PATENT DOCUMENTS

| 4,970,391 A | 11/1990 | Uber, III |
| 7,696,528 B2 | 4/2010 | Keller-Werdehausen et al. |

(Continued)

FOREIGN PATENT DOCUMENTS

| EP | 2664359 A1 | 11/2013 |
| WO | 2008148150 A1 | 12/2008 |

(Continued)

OTHER PUBLICATIONS

GE Healthcare. (2005). MR Field Notes: RF Coils . . . They've come a long, long way. (Year: 2005).*

(Continued)

*Primary Examiner* — Keith M Raymond
*Assistant Examiner* — Johnathan Maynard
(74) *Attorney, Agent, or Firm* — Sherry Austin (57) ABSTRACT

The invention provides for a magnetic resonance antenna assembly (100) comprising one or more antenna elements (106), wherein the magnetic resonance antenna assembly (106) further comprises multiple electronic dosimeters (108, 110, 204, 604) operable for measuring a cumulative radiation dose (470) of ionizing radiation (442) received by the magnetic resonance antenna assembly.

20 Claims, 8 Drawing Sheets (51) Int. Cl.
  *G01R 33/3415* (2006.01)
  *G01R 33/48* (2006.01)
  *A61B 5/055* (2006.01)
  *G01R 33/28* (2006.01)
  *A61N 5/06* (2006.01)

(52) U.S. Cl.
  CPC ......... *A61N 5/1075* (2013.01); *G01R 33/288* (2013.01); *G01R 33/34* (2013.01); *G01R 33/3415* (2013.01); *G01R 33/4808* (2013.01); *A61N 2005/0627* (2013.01); *A61N 2005/0628* (2013.01); *A61N 2005/1055* (2013.01); *G01R 33/28* (2013.01); *G01R 33/34046* (2013.01); *G01R 33/481* (2013.01); *G01R 33/4812* (2013.01)

(56) References Cited

U.S. PATENT DOCUMENTS

| | | | |
|---|---|---|---|
| 8,519,732 | B2 | 8/2013 | Kasper et al. |
| 2007/0016003 | A1* | 1/2007 | Piron ............ A61B 90/11 600/415 |
| 2009/0010390 | A1* | 1/2009 | Saoudi ............ A61N 5/1048 378/97 |
| 2011/0118588 | A1 | 5/2011 | Komblau |
| 2011/0260729 | A1 | 10/2011 | Carlone et al. |
| 2014/0021358 | A1* | 1/2014 | Wieringa ............ G01T 1/20 250/366 |
| 2014/0081068 | A1* | 3/2014 | Crijns ............ G01T 1/1603 600/1 |

FOREIGN PATENT DOCUMENTS

| | | |
|---|---|---|
| WO | 2012032477 A1 | 3/2012 |
| WO | 2012063158 A1 | 5/2012 |
| WO | 2014015421 A1 | 1/2014 |

OTHER PUBLICATIONS

Crijns, S., Raaymakers, B., Kok, J., Smit, K., Van Ouijen, J., & Lagendijk, J. (2011). Radiation induced RF coil degradation in hybrid MRI-accelerator systems. Proceedings of the International Society for Magnetic Resonance in Medicine. 19 (2011). (Year: 2011).*

Meijsing, I., Raaymakers, B. W., Raaijmakers, A. J. E., Kok, J. G. M., Hogeweg, L., Liu, B., & Lagendijk, J. J. (2009). Dosimetry for the MRI accelerator: the impact of a magnetic field on the response of a Farmer NE2571 ionization chamber. Physics in Medicine & Biology, 54(10), 2993. (Year: 2009).*

Hoogcarspel, S. J., Crijns, S. P., Lagendijk, J. J., Van Vulpen, M., & Raaymakers, B. W. (2013). The feasibility of using a conventional flexible RF coil for an online MR-guided radiotherapy treatment. Physics in Medicine & Biology, 58(6), 1925. (Year: 2013).*

GE Healthcare.(2005). MR Field Notes: RF Coils . . . They've come a long, long way. (Year: 2005).*

Simon, T. A., Kozelka, J., Simon, W. E., Kahler, D., Li, J., & Liu, C. (2010). Characterization of a multi-axis ion chamber array. Medical physics, 37(11), 6101-6111. (Year: 2010).*

Dong Wook Kim et al. "Risk of Second Cancer From Scattered Radiation of Intensity-Modulated Radiotherapies With Lung Cancer" Radiation Oncology, vol. 8, No. 1 Mar. 4, 2013, p. 47.

* cited by examiner

MAGNETIC RESONANCE ANTENNA WITH ELECTRONIC DOSIMETERS

CROSS REFERENCE TO RELATED APPLICATIONS

This application is a U.S. national phase application of International Application No. PCT/EP2015/054598, filed on Mar. 5, 2015, which claims the benefit of EP Application Serial No. 14159359.0 filed on Mar. 13, 2014 and is incorporated herein by reference.

TECHNICAL FIELD

The invention relates to systems for magnetic resonance guided radiotherapy, in particular to the construction of antenna assemblies.

BACKGROUND OF THE INVENTION

Integration of magnetic resonnace imaging and radiotherapy opens new horizons in Radiotherapy by improved lesion targeting, especially for moving organs.

The combination of magnetic resonance apparatuses and radiotherapy sources is known. Typically a radiation source is placed on a rotating gantry about the magnet and the magnet designed such that the radiation passes through the magnet or through a space in the magnet or between multiple magnets. United States patent application US 2011/0260729 A1 discloses a magnetic resonance imaging apparatus suitable for radiotherapy.

Various components such as electronic components can be damaged over time as they are exposed to radiation. U.S. Pat. No. 8,519,732 B2 discloses monitoring the weak light emissions emitted during the breakdown of a pn-junction to use as a self test for breakdown during the operation of the semiconductor component due to radiation.

SUMMARY OF THE INVENTION

The invention provides for a magnetic resonance antenna assembly, a medical instrument, and a method of operating a medical instrument in the independent claims. Embodiments are given in the dependent claims.

As will be appreciated by one skilled in the art, aspects of the present invention may be embodied as an apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wire line, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bi-stable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Medical image data is defined herein as two or three dimensional data that has been acquired using a medical imaging scanner. A medical imaging scanner is defined herein as an apparatus adapted for acquiring information about the physical structure of a patient and construct sets of two dimensional or three dimensional medical image data. Medical image data can be used to construct visualizations which are useful for diagnosis by a physician. This visualization can be performed using a computer.

Magnetic resonance data is an example of medical image data. Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

Nuclear medical imaging data is a further example of medical image data. Nuclear medical image data is data acquired using a nuclear medical imaging technique such as Positron Emission Tomography (PET) or Single Photon Emission Tomography (SPECT). A nuclear medical image as used herein encompasses the reconstructed two or three dimensional visualization of radio-nucleotide concentration reconstructed from nuclear medical imaging data. This visualization can be performed using a computer.

In one aspect the invention provides for a magnetic resonance antenna assembly comprising one or more antenna elements. An antenna element as used herein encompasses a portion of an antenna that is actively used for the reception or transmission of radio-frequency signals. A magnetic resonance antenna assembly is an antenna assembly that is used or intended for use in performing a magnetic resonance imaging method or may be incorporated into a magnetic resonance imaging system. The magnetic resonance antenna assembly further comprises multiple electronic dosimeters operable for measuring a cumulative radiation dose of ionizing radiation received by the magnetic resonance antenna assembly. An electronic dosimeter as used herein encompasses a dosimeter or radiation detector and accompanying electronics which measure the dose of radiation actively. An example of an electronic dosimeter is a silicon-based radiation detector. The silicon-based detector may be combined with electronics for measuring the cumulative radiation dose. This example may have the benefit that the radiation received by the magnetic resonance antenna assembly can be measured and therefore the dosage of radiation to the antenna assembly is known. This may be useful in predicting when the magnetic resonance antenna assembly will fail or when it may be useful to replace it before it fails.

In some examples the cumulative radiation dose to the magnetic resonance antenna assembly may be determined spatially. For instance a number of electronic dosimeters could be distributed in different places or positions in the magnetic resonance antenna assembly so that a model or estimate of the radiation received in various regions is known.

In another embodiment the magnetic resonance antenna assembly comprises an antenna element support operable for supporting the one or more antenna elements. The multiple electronic dosimeters comprise a set of antenna element dosimeters. The antenna element dosimeters are distributed within the antenna element support. This embodiment may be beneficial because the cumulative radiation dose to the antenna elements and the antenna element support may enable prediction of when the functioning of the antenna element fails. For instance ionizing radiation may destroy or degrade the material which the antenna element support is constructed from.

The antenna element support in some examples may be considered the structure for holding or supporting the antenna elements. In some examples the antenna element support may be rigid, for instance as used for a head coil. In other examples the antenna element support may be flexible and in which case the magnetic resonance antenna assembly forms a surface coil which is operable to be placed on a surface of the patient.

In another embodiment the magnetic resonance antenna assembly further comprises a radio-frequency control component for distributing radio-frequency power to the one or more antenna elements and/or for receiving a radio-frequency signal from the one or more antenna elements. The antenna elements may in some examples be driven separately and different amplitudes and/or phase of radio-frequency power are supplied to the different antenna elements. The radio-frequency control component may comprise such components as equipment for splitting a radio-frequency signal to different antenna elements; it may comprise a matching network for each of the antenna elements or for the antenna elements as a whole.

The multiple electronic dosimeters comprise a set of control component dosimeters. The control component dosimeters are distributed in the vicinity of electronics which make up the radio-frequency control component. The control component dosimeters are therefore positioned within the radio-frequency control component. This embodiment may be beneficial because it enables the measurement of a radiation dose to the electronic components which make up the radio-frequency control component. This may enable accurate determination or prediction of when the radio-frequency control component will fail due to ionizing radiation.

In another embodiment the radio-frequency control component is detachable from the magnetic resonance antenna assembly. This embodiment may be beneficial because the radio-frequency control component may be replaceable separate from the other components of the magnetic resonance antenna assembly such as the antenna element support and the one or more antenna elements. The various components may receive differing amounts of radiation and may therefore fail at different times or need to be replaced at different times. Making the separate pieces modular or replaceable like this enables only replacing those components which are known to have been damaged by radiation.

In another embodiment the radio-frequency control component is removed from the magnetic resonance antenna assembly. This may be beneficial because the radio-frequency control component may be placed remotely enough so that it receives less radiation.

In another embodiment the magnetic resonance antenna assembly further comprises a dosimeter controller. The dosimeter controller is operable for electrically powering each of the multiple electronic dosimeters. The dosimeter controller is operable for determining the accumulative radiation dose using the multiple electronic dosimeters. This embodiment may be beneficial because it provides electronics for modifying simple radiation detectors and using them as dosimeters.

In another embodiment the dosimeter controller is operable for executing an antenna failure model. The antenna failure model is operable for predicting the failure of the magnetic resonance antenna assembly using the cumulative radiation dose. The antenna failure model uses the cumulative dose whether it is spatial or not as input to a model. In some examples the dosimeter controller is a standalone unit. In other examples the dosimeter controller may be for instance partially comprise a computer or data processing system. The controller could therefore include a processor on a magnetic resonance imaging system in some examples.

In another aspect the invention provides for a medical instrument comprising a magnetic resonance imaging system for acquiring magnetic resonance data from a subject at least partially within an imaging zone. The imaging zone as used herein encompasses a region where the magnetic field is sufficiently high and uniform enough for performing magnetic resonance imaging. The magnetic resonance imaging system further comprises a magnetic resonance antenna assembly according to an embodiment. The medical instrument is operable for acquiring the magnetic resonance data using the magnetic resonance antenna assembly.

In some examples the magnetic resonance antenna assembly is the embodiment where the dosimeter controller is operable for executing an antenna failure model and the antenna failure model is operable for predicting the failure of the magnetic resonance antenna assembly using the cumulative radiation dose.

In another embodiment the medical instrument further comprises a main magnet operable for generating a main magnetic field. The main magnetic field is a magnetic field which is strong enough and has a region which is uniform enough for performing magnetic resonance imaging. The imaging zone is the region in which the main magnetic field is sufficiently strong and uniform enough for performing magnetic resonance imaging. The medical instrument further comprises one or more magnet electronic dosimeters attached to the main magnet. The one or more magnet electronic dosimeters are operable for measuring scattered ionizing radiation within the main magnetic field.

The dosimeter controller is operable for electrically powering each of the magnet electronic dosimeters. The dosimeter controller is further operable for determining the cumulative radiation dose using the one or more magnet electronic dosimeters. The magnet electronic dosimeters are additional or separate electronic dosimeters which are used as input so that the field of radiation dose is more accurately determined. This may be used for additional input for an antenna failure model. This may enable more accurate determination of when the magnetic resonance antenna assembly or a portion of the magnetic resonance antenna assembly should be replaced. Notably, in the embodiment that the magnet electronic dosimeters are separate electronic dosimeters, these separate magnet electronic dosimeters determine the field of radiation dose. From this field of radiation dose, the cumulative radiation dose at the antenna elements and/or at the radio frequency control component on the antenna support can be estimated. Then, a fair expectation of failure due to the cumulative radiation does received by the antenna elements and the radio frequency control is obtained without the need for antenna element dosimeters and control component dosimeters. Further, the field of radiation dose measured by the magnet electronic dosimeters can be employed to estimate the cumulative radiation dose received by other accessories or auxiliary devices that may be used within the magnet bore and accordingly make a fair estimate of the expected failure of such accessories or auxiliary devices. Further the field of radiation dose measured by the magnet electronic dosimeters can be used as additional electronic dosimeters together with the measurements by the antenna element dosimeters and the control component dosimeters to achieve a higher degree of redundancy for estimating the cumulative radiation dose at the antenna elements and at the radio frequency control components.

In another embodiment the medical instrument further comprises one or more subject electronic dosimeters operable for being placed on a subject at least partially within the imaging zone. The subject is placed at least partially within the imaging zone and the portion of the subject within the imaging zone is then able to be imaged by the magnetic resonance imaging system. The one or more subject electronic dosimeters is operable for measuring scattered ionizing radiation. The dosimeter controller is operable for electrically powering each of the one or more subject electronic dosimeters. The dosimeter controller is further operable for determining the cumulative radiation dose using the one or more subject electronic dosimeters. Having additional electronic dosimeters placed on the subject may enable more accurate operation of the dosimeter controller or a better prediction of the cumulative radiation dose thereby making it more accurate as to when to replace the entire or a portion of the magnetic resonance antenna assembly.

In another embodiment the radiation therapy device is a gamma knife.

In another embodiment the radiation therapy device is a gamma beam radiation system.

In another embodiment the radiation therapy device is a charged particle beam irradiation system.

In another embodiment the radiation therapy device is a linear accelerator or LINAC.

In another embodiment the radiation therapy device is an X-ray beam irradiation system.

In another embodiment the medical instrument further comprises a medical nuclear imaging system operable for reconstructing a nuclear medical image from an imaging volume. The imaging volume is within the imaging zone. The imaging volume is for a positron emission tomography or other nuclear magnetic imaging technique system and the imaging volume is for the magnetic resonance imaging system. The medical instrument can therefore perform both a nuclear imaging technique and magnetic resonance imaging simultaneously.

In another embodiment the medical instrument further comprises a user interface. The user interface is operable for displaying a warning message when the antenna failure model predicts the failure of the magnetic resonance antenna assembly. This may be useful because it may inform an operator or other user of the medical instrument when to replace the entire or a portion of the magnetic resonance antenna assembly.

In another aspect the invention provides for a method of operating a medical instrument. The magnetic resonance imaging system is operable for acquiring magnetic resonance data from an imaging zone using a magnetic resonance antenna assembly according to an embodiment. The medical instrument comprises a magnetic resonance imaging system and a radiation therapy device. The method comprises controlling the magnetic resonance imaging system to acquiring magnetic resonance data using the magnetic resonance antenna assembly. The method further comprises controlling the radiation therapy device to irradiate a target zone within the imaging zone using ionizing radiation. The method further comprises measuring the cumulative radiation dose using the multiple electronic dosimeters during irradiation of the target zone.

The method further comprises predicting a failure of the magnetic resonance antenna using an antenna failure model. The antenna failure model is operable for predicting the failure of the cumulative radiation dose. The antenna failure model for instance may be something which is accurately determined by purposely irradiating a magnetic resonance antenna assembly using ionizing radiation until it fails. The method may also be a computer implemented method. The method may also be implemented in the form of executable instructions which cause a processor to control the medical instrument to perform all steps of the method.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Conventionally, preparative diagnostic imaging and radiation therapy (RT) are carried out sequentially. This is true especially if MR imaging is used for RT planning. For combined MR/RT systems it is beneficial if the RF-coils are compatible with the harsh RT environment. Examples may provide for a modular RF-coil concept with integrated health-check. Integrated dosimeters in MR system-body coil or surface coils measure accumulated radiation. Local sensitive electronic modules may be replaced in some examples once a defined radiation dose has been reached, such that quality and safety is guaranteed and cost for service is reduced.

For the radiation therapy the patient is placed in the RT system and fixated. A low resolution X-ray is done and the pre-acquired high resolution data is morphed onto the actual X-ray data. The dose plan is modified accordingly and the therapy is carried out.

Conventional RF-coils are not designed to withstand the harsh environment of a radiation therapy system. Coil electronics is delicate and materials typically are not tested for high doses of ionizing radiation. Moreover coils are required to operate flawlessly over a long period of time under these conditions.

Examples may provide for modified RF-coils especially designed for use in an MR/RT environment. The coil is separated such that only those parts of the coil remain in the RT field of view which are absolutely necessary (e.g. PIN diodes for detuning, cabling, lumped capacitors, . . . ). Preamps and other electronics are placed remote such that the dose hitting those components is significantly lower.

In some examples, the coil and the electronics module, carry dosimeter. These dosimeters measure the accumulated dose, are read out and the result is e.g. compared for example to pre-acquired lookup tables of material lifetime vs. dose. In case of a looming failure because of excessive dose, this self-check can indicate the status of the coil and timely replacement of coil or subcomponents.

A central element of some examples is a RF-coil for MR/RT with integrated dosimeter that can measure the accumulated dose at different parts of the coil. The dosimeter is read out via an extra cable or optically. The generated dose is compared to pre-acquired lookup tables in which material-health vs. dose values are stored. This self check can indicate if and when the coil or parts of the coil are about to fail and when a replacement is needed. In a first embodiment the coil or coil array is split such that all delicate electronics like preamps, RXE-modules, coil drivers and the like are placed remotely from the actual coil conductors (see FIG. 1).

Figure 1:
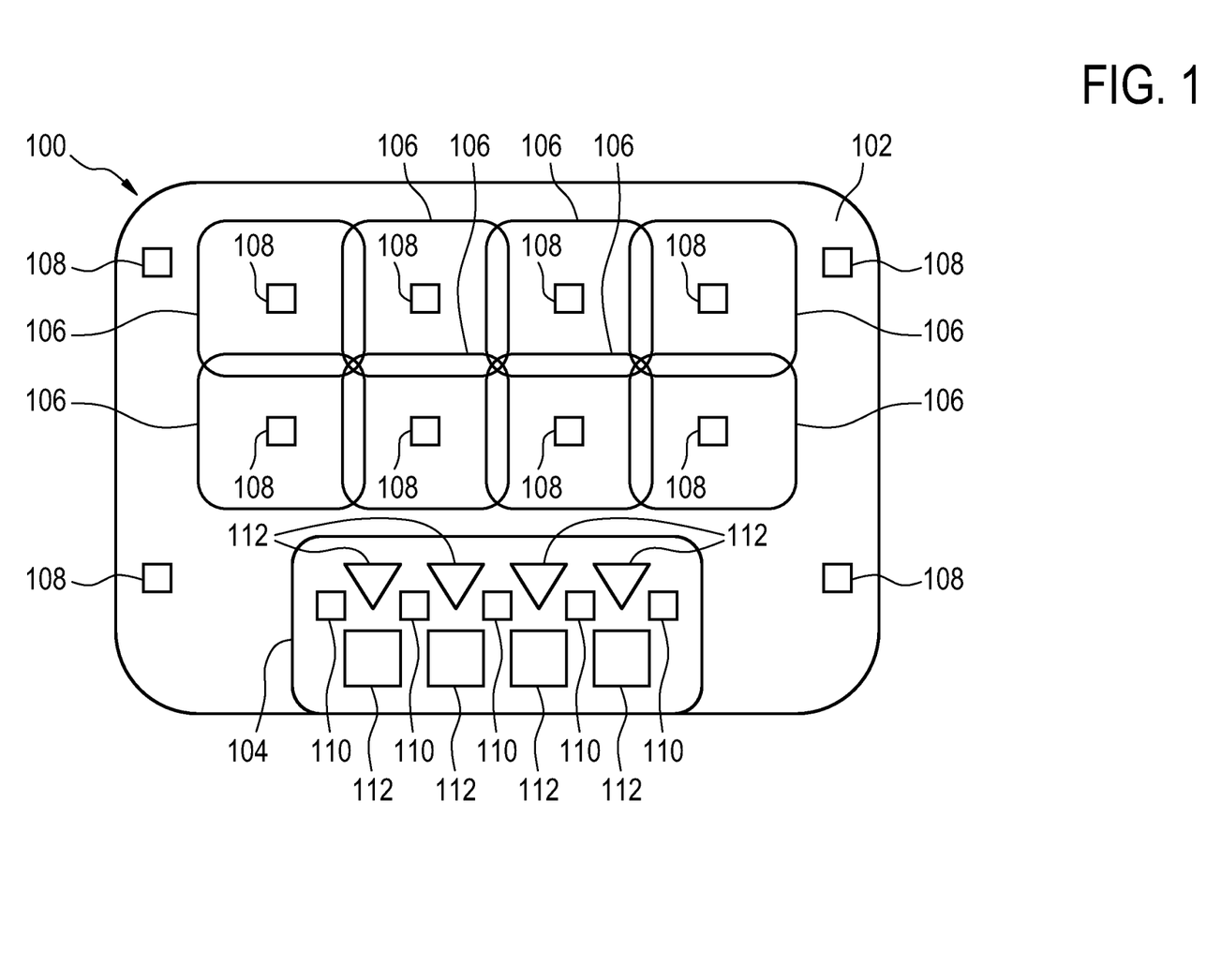
FIG. 1 shows an example of a magnetic resonance antenna assembly.

FIG. 1 shows an example of a magnetic resonance antenna assembly 100. The magnetic resonance antenna assembly 100 comprises an antenna element support 102. Attached to the antenna element support 102 is a radio-frequency control component 104. There are a number of antenna elements 106 which are either embedded into or attached to the antenna element support 102. In the antenna element support there are a number of antenna element dosimeters 108. The radio-frequency control component 104 could for example for a receive coil be pre-amplification electronics which are attached to each of the antenna elements 106. In other examples the radio-frequency control component 104 could be a set of matching networks for connecting to each of the antenna elements 106. Within the radio-frequency control component 104 is shown a number of control component dosimeters 110 distributed amongst electronic components 112.

In some examples the radio-frequency control component 104 is removable from the antenna element support 102. A socket or connector may be used in this case for connecting the output of the radio-frequency control component 104 to the various antenna elements 106. The antenna element dosimeters 108 and the control component dosimeters 110 make up the electronic dosimeters. The example shown in FIG. 1 for instance may be a surface coil. However, other standard configurations of magnetic resonance antennas are also applicable.

In this way the coil itself is exposed to high radiation levels while the more valuable electronics has more protection. Both parts may carry the dosimeters described. In this way it can be decided independently, if one part needs to be replaced. The described setup thus saves cost since the electronics may be operated longer than the actual coil before the 'lethal' dose has been accumulated and failure occur.

In another example local electronics, which is exposed to radiation has integrated radiation sensors, thus measuring the integrated dose of the local electronics module. The local electronic module is replaced when the accumulated dose is achieved. The module can be replaced before active electronic components start to fail. This is depicted in FIG. 2, which shows a integrated MRI body coil with replaceable electronics modules.

Figure 2:
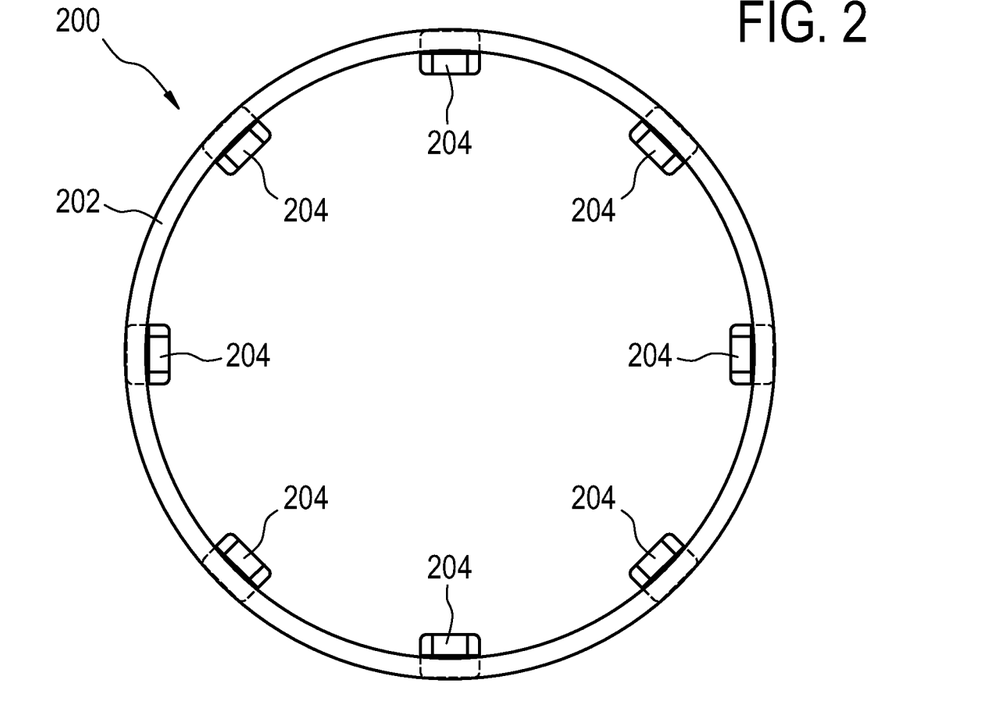
FIG. 2 shows a further example of a magnetic resonance antenna assembly.

FIG. 2 shows a further example of a magnetic resonance antenna assembly. The magnetic resonance antenna assembly 200 comprises a magnetic resonance body coil 202. In the interior of the body coil 202 there are a number of electronic dosimeters 204 distributed. In some examples the electronic dosimeters are sensors which are attached to a central electronics unit. In another example the entire electronic dosimeter 204 comprises the radiation sensor and also drive electronics and electronics for recording the cumulative radiation dose.

Figure 3:
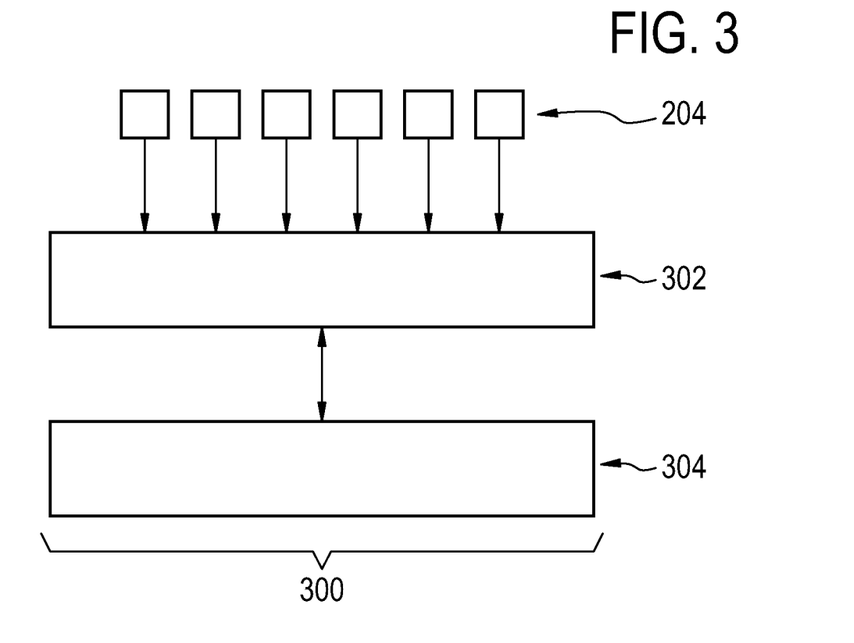
FIG. 3 shows an example of a dosimeter system.

Radiation sensors are connected to a HW control and an integrated software algorithm manages the sensor data and report the status to the MRI console and finally to the MR service personnel, which can then replace modules on time (see FIG. 3).

FIG. 3 shows an example of a dosimeter system 300. The system 300 comprises a number of electronic dosimeters 204. The electronic dosimeters 204 are connected to a dosimeter controller which functions as for sensor control and for memory recording the cumulative radiation dose. The dosimeter controller 302 is connected to a magnetic resonance imaging system controller or a computer 304. The controller 304 may function as a control system for an entire magnetic resonance imaging system.

In another example the sensors are not located in the coil or the electronics but at a certain position within the bore. For each RT-session the sensor has to be placed such that is it located close to the RF-coil used. This setup can be seen as an intermediate step since the measured dose is not exactly that, seen by the coil. On the other hand, conventional coils may be used and the measured doses are regarded as a lower bound to the real dose experienced by the coil.

Figure 4:
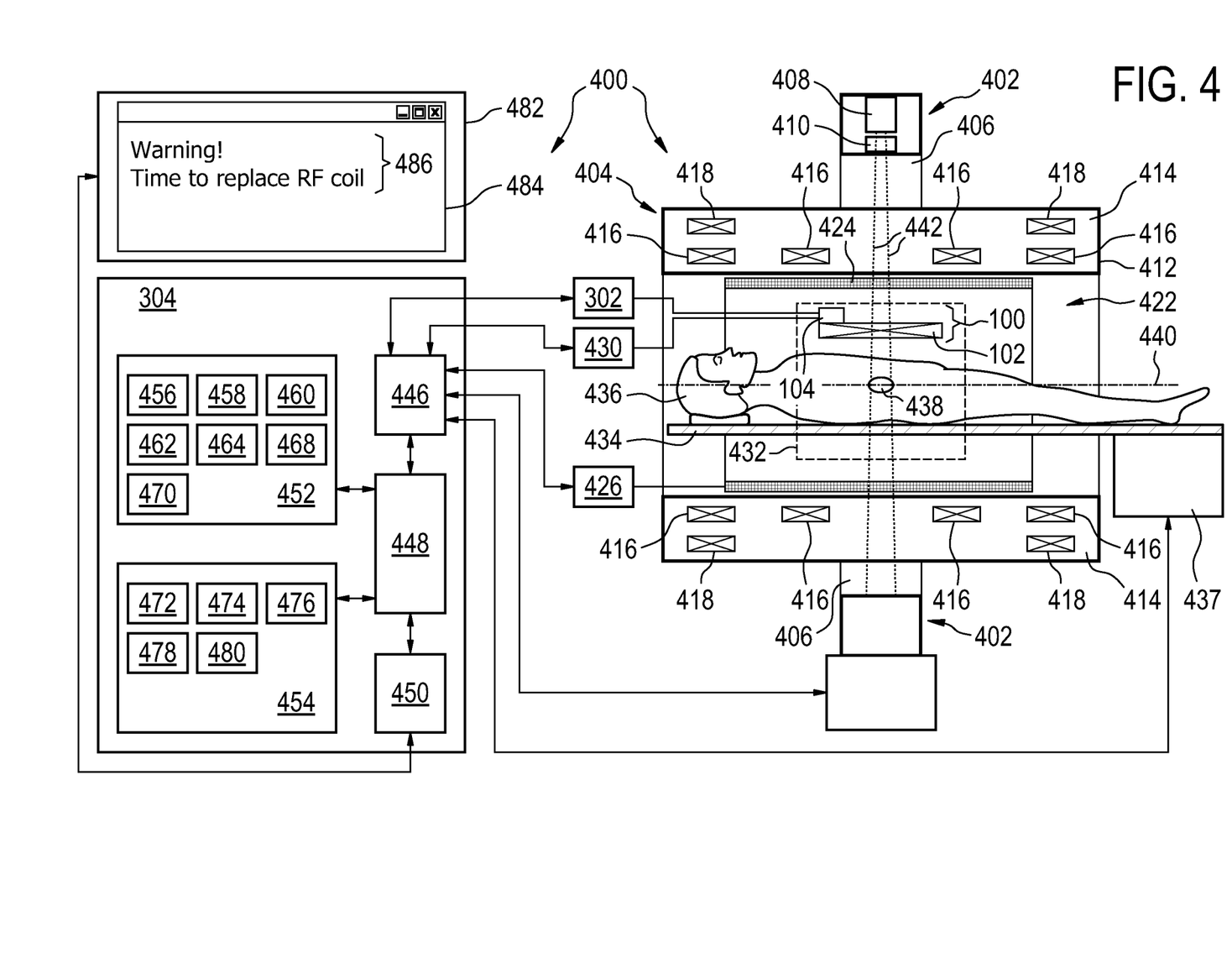
FIG. 4 shows an embodiment of a medical instrument.

FIG. 4 shows an embodiment of a medical instrument 400. The medical instrument 400 comprises a external beam radiotherapy system 402 and a magnetic resonance imaging system 404. The external beam radiotherapy system 402 comprises a gantry 406 and a radiotherapy source 408. The gantry 406 is for rotating the radiotherapy source 408 about an axis of gantry rotation 440. Adjacent to the radiotherapy source 408 is a collimator 410. The magnetic resonance imaging system 404 comprises a magnet 412.

It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore of the cylindrical magnet there is an imaging zone where the magnetic field is strong and uniform enough to perform magnetic resonance imaging.

The magnet 412 shown in this embodiment is a standard cylindrical superconducting magnet. The magnet 412 has a cryostat 414 with superconducting coils within it 416. There are also superconducting shield coils 418 within the cryostat also. The magnet 412 has a bore 422.

Within the bore of the magnet is a magnetic field gradient coil 424 for acquisition of magnetic resonance data to spatially encode magnetic spins within an imaging zone of the magnet. The magnetic field gradient coil 424 is connected to a magnetic field gradient coil power supply 426. The magnetic field gradient coil 424 is intended to be representative, to allow radiation to pass through without being attenuated it will normally be a split-coil design. Typically magnetic field gradient coils contain three separate sets of coils for spatially encoding in three orthogonal spatial directions. The magnetic field gradient power supply 426 supplies current to the magnetic field gradient coils. The current supplied to the magnetic field coils is controlled as a function of time and may be ramped or pulsed.

There is a magnetic resonance antenna assembly 100 connected to a transceiver 430. The magnetic resonace antenna assembly 100 is adjacent to an imaging zone 432 of the magnet 412. The imaging zone 432 has a region of high magnetic field and homogeneity which is sufficient for performing magnetic resonance imaging. The radio frequency coil 428 may is for manipulating the orientations of magnetic spins within the imaging zone and for receiving radio transmissions from spins also within the imaging zone. The magnetic resonance antenna assembly 100 may also be referred to as an antenna or channel. magnetic resonance antenna assembly 100 may contain multiple coil elements. The radio frequency antenna assembly 100 comprises the components shown in FIG. 1. A dosimeter controller 302 is also connected to the radio frequency antenna assembly 100 and a computer 304 as is shown in FIG. 3.

The radio frequency coil 428 and radio frequency transceiver 430 may be replaced by separate transmit and receive coils and a separate transmitter and receiver. It is understood that the radio frequency coil and the radio frequency transceiver are representative. The radio frequency antenna is intended to also represent a dedicated transmit antenna and a dedicated receive antenna. Likewise the transceiver may also represent a separate transmitter and receivers.

Also within the bore of the magnet 422 is a subject support 434 for supporting a subject 436. The subject support 434 may be positioned by a mechanical positioning system 437. Within the subject 436 there is a target zone 438. The axis of gantry rotation 440 is coaxial in this particular embodiment with the cylindrical axis of the magnet 412. The subject support 434 has been positioned such that the target zone 438 lies on the axis 440 of gantry rotation. The radiation source 408 is shown as generating a radiation beam 442 which passes through the collimator 410 and through the target zone 438. As the radiation source 408 is rotated about the axis 440 the target zone 438 will always be targeted by the radiation beam 442. The radiation beam 442 passes through the cryostat 414 of the magnet. The magnetic field gradient coil may have a gap which separate the magnetic field gradient coil into two sections. If present, this gap reduces attenuation of the radiation beam 442 by the magnetic field gradient coil 424. In some embodiments the radio frequency coil 428 may also have gaps or be separated to reduce attenuation of the radiation beam 442.

The transceiver 430, the magnetic field gradient coil power supply 426 and the mechanical positioning system 437 are all shown as being connected to a hardware interface 446 of a computer system 304. The computer system 304 is shown as further comprising a processor 448 for executing machine executable instructions and for controlling the operation and function of the therapeutic apparatus. The hardware interface 446 enables the processor 448 to interact with and control the medical instrument 400. The processor 448 is shown as further being connected to a user interface 450, computer storage 452, and computer memory 454.

The computer storage 452 is shown as containing a collection of pulse sequences 456. A pulse sequence as used herein encompasses a sequence of commands the processor 448 may use to control the magnetic resonance imaging system 404 to acquire magnetic resonance data. The computer storage 452 is shown as further containing magnetic resonance data 458 which is acquired using the pulse sequence 456. The computer storage 452 is further shown as containing a magnetic resonance image 460 which is reconstructed from the magnetic resonance data 458. The computer storage 452 is further shown as containing planning data 462. The planning data 462 for instance could be received via an external network connection, a thumb drive, or even be entered via the user interface 450. The computer storage 452 is further shown as containing a planning data registration 464 which contains the registration between the planning data 462 and the first magnetic resonance image 460. The computer storage 452 is further shown as containing an external beam dosage plan 468. The computer storage 452 is further shown as containing a cumulative radiation dose 470 measured with the electronic dosimeters shown in the magnetic resonance antenna assembly 100. In some examples the cumulative radiation dose is stored by the dosimeter controller 302.

The computer memory 454 is shown as containing a control module 472. The control module 472 contains computer-executable code which enables the processor 448 to control the operation and function of the medical instrument 400. The computer memory 454 is shown as further containing an image reconstruction module 474 which enables the processor 448 to reconstruct magnetic resonance data 458 into the magnetic resonance image 460. The computer memory 454 is further shown as containing an image registration module 476 which is operable for performing image registration between two images or data descriptive of an image and an image. For example the image registration module 476 contains computer-executable code which enables the processor 448 to register the planning data 462 to the first magnetic resonance image 460. The computer memory 454 is further shown as containing a radiotherapy planning module 478 which was used to generate the external beam dosage plan 468 using the spatially dependent radiation dose within the planning data 462 and the first magnetic resonance image 460. It is of course implicit that the registration 464 may also be used by the radiotherapy planning module 478. The computer memory is further shown as containing an antenna failure model 480 which uses the cumulative radiation dose 470 to predict the failure of a portion of all of the magnetic resonance assembly due to radiation 442. In some examples, the antenna failure model 480 is executed by the dosimeter controller.

The user interface 450 is shown as optionally being connected to a monitor or display 482, which is operable to display a graphical user interface 484. When the antenna failure model 480 predicts a failure or partial failure of the magnetic resonance antenna assembly 100 a warning 486 may be displayed in the graphical user interface 484.

The computer memory 454 may contain additional software modules. For instance it may contain a software module to generate commands for controlling the external beam radiotherapy system using the external beam dosage plan. The memory may also contain a software module for modifying the external beam dosage plan and/or the commands for controlling the externally beam radiotherapy system using monitoring magnetic resonance data.

Figure 5:
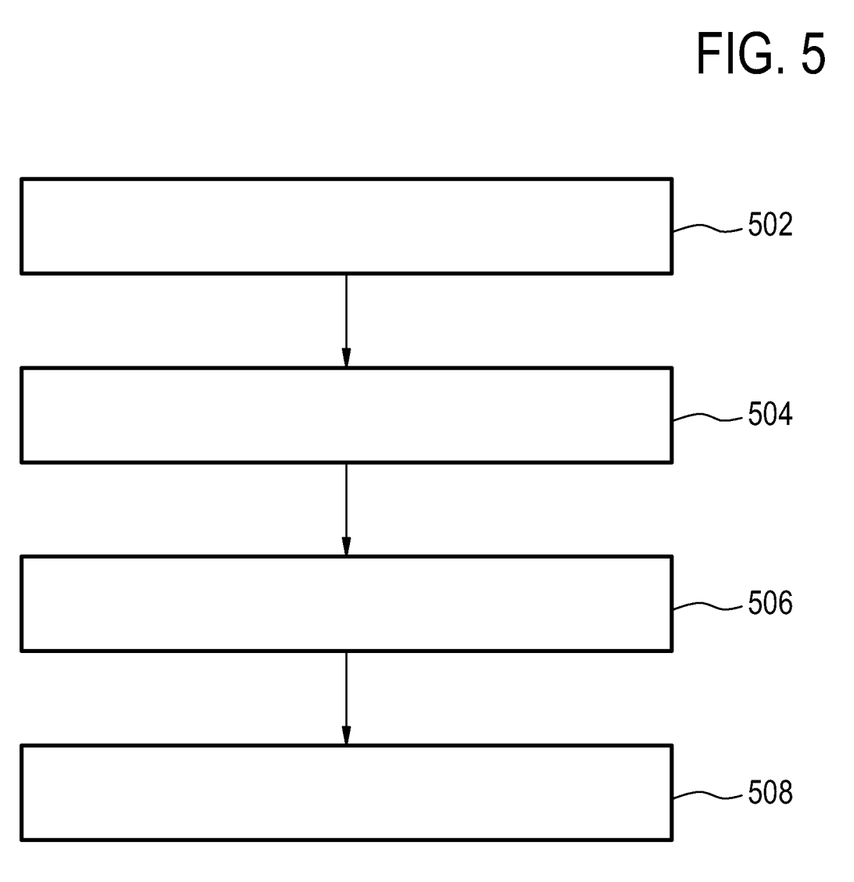
FIG. 5 shows a flowchart which shows a method of operating the medical apparatus of FIG. 4.

FIG. 5 shows a flowchart which shows a method of operating the medical apparatus 400 of FIG. 4. First, in an optional step a subject 436 is placed into the magnetic resonance imaging system 404. Next in step 502 magnetic resonance data is acquired using the magnetic resonance antenna assembly 100. Next in step 504 a target zone 438 is irradiated within the imaging zone 432 using ionizing radiation 442. Next in step 506 the cumulative radiation dose 470 is measured using the multiple electronic dosimeters during irradiation of the target zone. Finally in step 508 a prediction of failure 486 of the magnetic resonance antenna assembly 100 using an antenna failure model 480. The antenna failure model 480 is operable for predicting the failure using the cumulative radiation dose 470.

Figure 6:
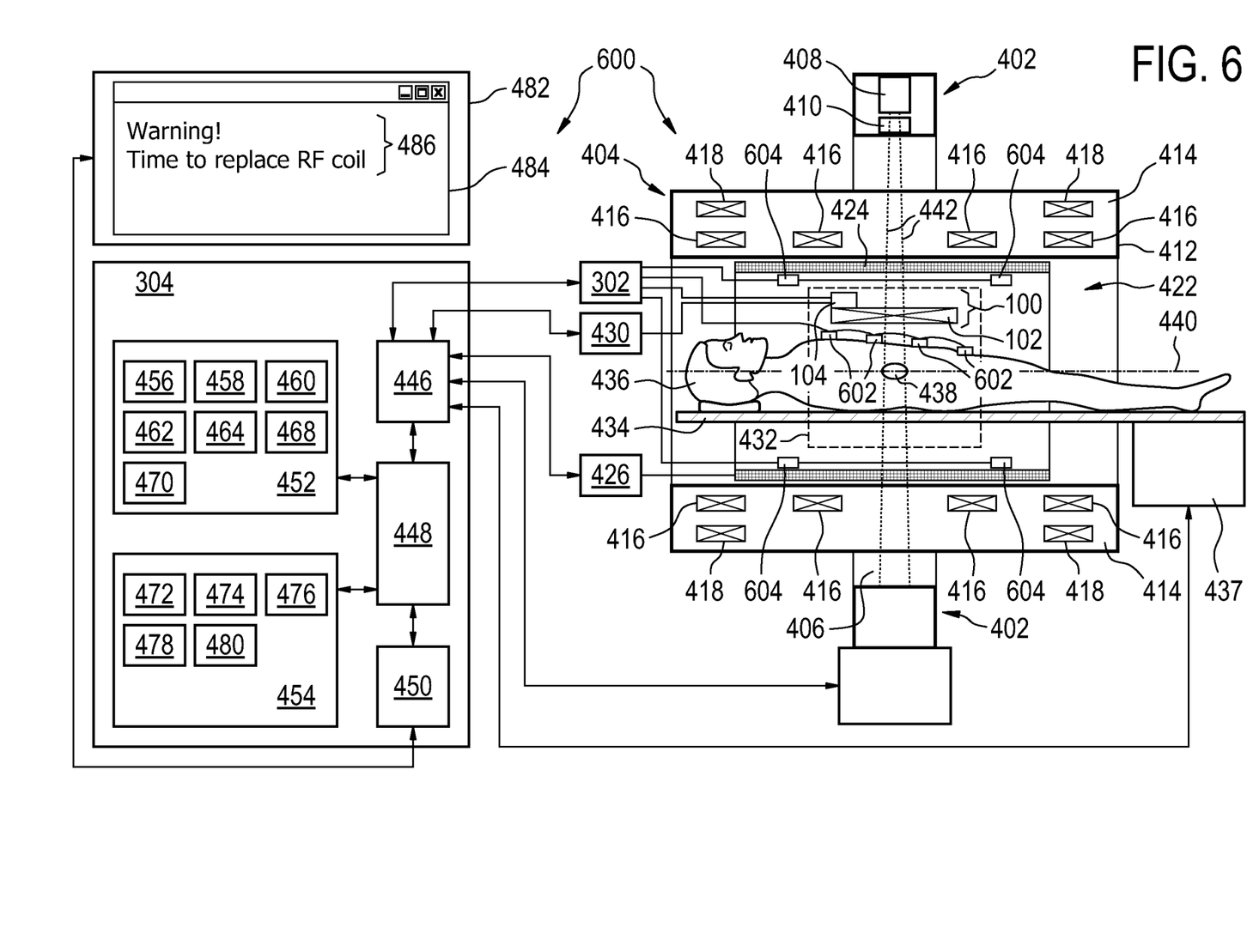
FIG. 6 shows a further example of a medical instrument.

FIG. 6 shows a further example of a medical instrument 600. The medical instrument 600 of FIG. 6 is similar to the medical instrument 400 of FIG. 4. Additional electronic dosimeters have been placed into the system. Shown in the Fig. is a number of subject electronic dosimeters 602 placed on a surface of the subject 436. These may be placed in the radiation beam path 442 or in an area surrounding it so that the radiation beam 442 and/or the scattered radiation may be measured with the subject electronic dosimeters 602. Also shown are a number of magnet electronic dosimeters 604 which are attached to the inside of the bore 442 of the magnet 412. The placement of the magnet electronic dosimeters 604 is intended to be representative and is not drawn to scale. It is very likely that in an actual implementation the magnet dosimeters 604 would be placed adjacent to the beam path 442. The magnet electronic dosimeters 604 would also be useful for measuring scattered radiation. The dosimeters 602 and 604 are shown as being connected to the dosimeter controller 302. The data from these dosimeters 602, 604 is also incorporated into the cumulative radiation dose 470 and make predictions by the antenna failure model 480 more accurate.

Figure 7:
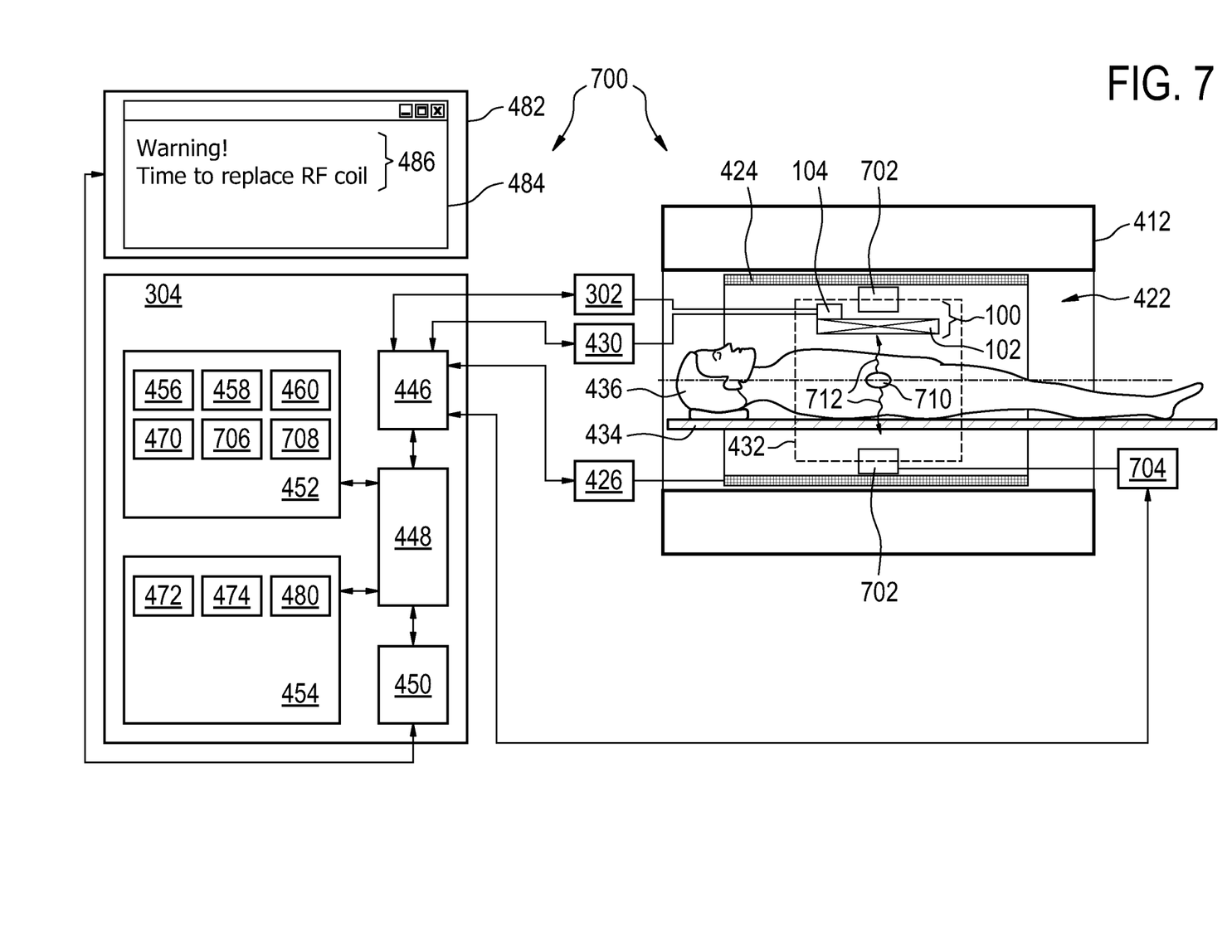
FIG. 7 shows a further example of a medical instrument.

FIG. 7 shows a further example of a medical instrument 700. The medical instrument 700 in FIG. 7 is similar to the medical instrument 400 in FIG. 4 except the external beam radiotherapy system 402 and the components and code and software and data related to it have been removed. In its place a nuclear medical imaging system which comprises a sensor ring 702 and control electronics 704 has been installed instead. This type of sensor ring 702 could for instance be used for positron emission tomography or single photon emission tomography. The electronics 704 either drive radiation sensors in the ring 702 which can function in a high magnetic field or else light pipes or fiber optics are used to bring light from scintillators outside to light detectors in the electronics 704.

Data recorded by the electronics 704 is recorded as nuclear medical imaging data 706. The image reconstruction module 474 is able to reconstruct the nuclear medical imaging data 706 into a nuclear medical image 708. In this example the magnetic resonance data 458 is normal magnetic resonance imaging data which is used to reconstruct a magnetic resonance image 460 using the image reconstruction module 474. The medical imaging ring 702 functions by detecting radiation 712 emitted by a concentration of radio isotope 710 within the body of the subject 436. The medical instrument 700 is able to simultaneously do magnetic resonance imaging and a medical imaging technique at the same time.

Figure 8:
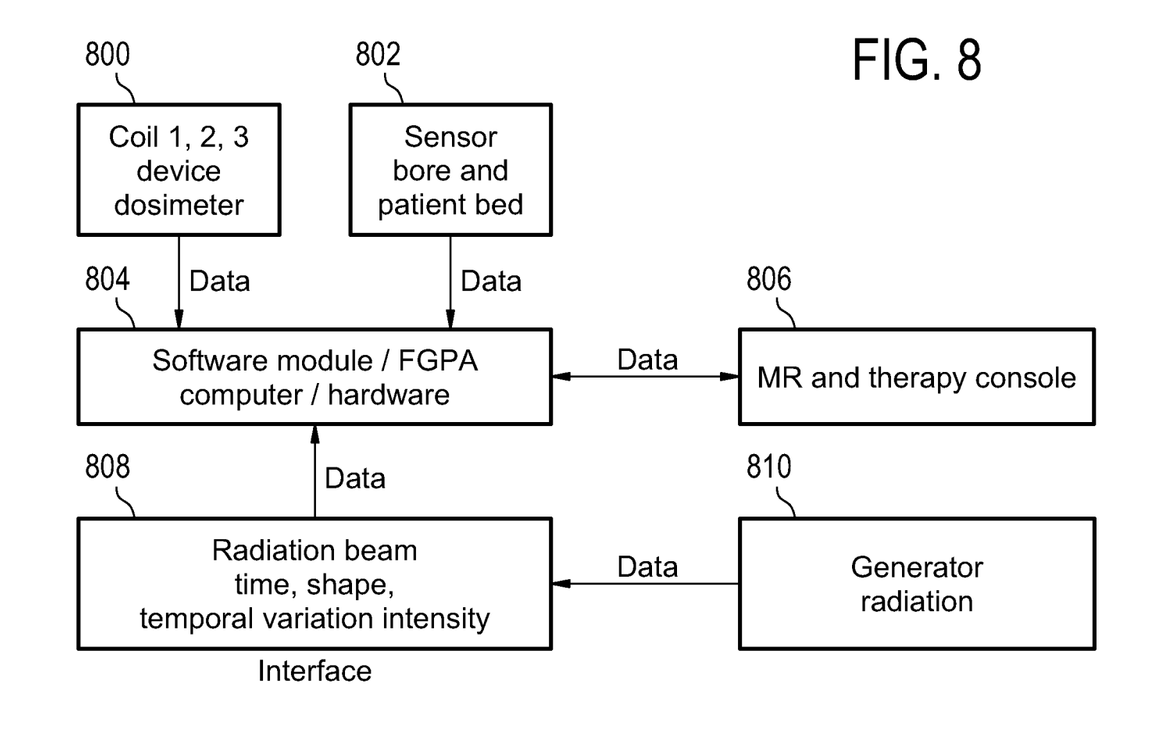
FIG. 8 shows a schematic diagram how the antenna failure model 480 may function in some examples.

FIG. 8 shows a schematic diagram how the antenna failure model 480 may function in some examples. Not all data depicted in FIG. 8 or its function is used in every example. Block 800 represents data from multiple electronic dosimeters of the magnetic resonance antenna assembly. Block 802 is optional and represents data acquired by subject electronic dosimeters and/or magnetic electronic dosimeters. The block 804 represents a software module executed on a computer or FPGAs which are programmed with the antenna failure model 480. Some examples also feed data from the magnetic resonance and/or therapy control console 806. Such things as data about the particular radiation therapy protocol and/or the imaging protocol may also be incorporated into the model 804. In the case where there is a radiation beam generator the generator radiation 810 supplies data to the radiation beam system 808. Block 808 represents an interface 808 to the radiation generator 810. Then data descriptive of the radiation beam such as the duration of the beam, the shape, the temporal variation and the intensity may also be fed to the model 804. Depending upon the complexity of the model all these various sources of data may be supplied to the antenna failure model 480.

Figure 9:
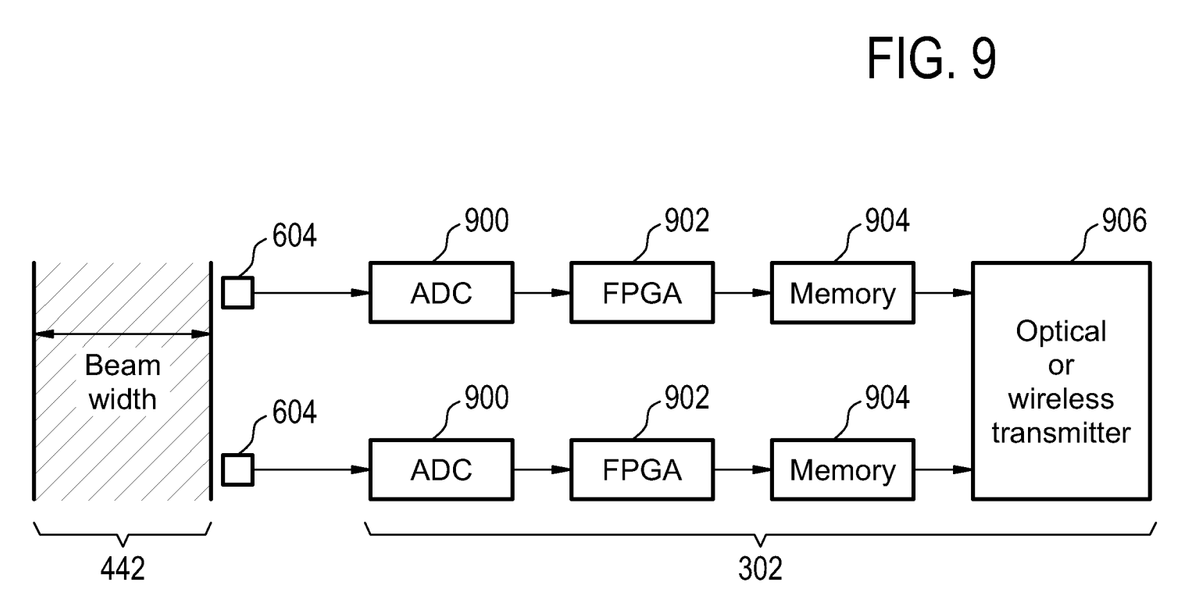
FIG. 9 shows an example of how the dosimeter controller 302 may be implemented in some cases.

FIG. 9 shows an example of how the dosimeter controller 302 may be implemented in some cases. The area 442 represents the radiation beam. Adjacent to the beam width there are shown several magnet electronic dosimeters 604. However, the dosimeter 604 may also be subject to electronic dosimeters or also some of the multiple electronic dosimeters of the magnetic resonance antenna assembly. Each dosimeter 604 is connected to an analyzer digital controller converter 900. The ADC 900 then feeds its data to an FPGA 902. This determines the dose received over time. This dose information is then stored in a memory 904. The memory 904 transfers data to the magnetic resonance imaging system via an optical or wireless transmitter 906.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE NUMERALS 100 magnetic resonance antenna assembly
102 antenna element support
104 radio frequency control component
106 antenna elements
108 antenna element dosimeters
110 control component dosimeters
112 electronic component
200 magnetic resonance antenna assembly
202 magnetic resonance body coil
204 electronic dosimeter
300 dosimeter system
302 dosimeter controller
304 magnetic resonance imaging system controller or computer
400 medical instrument
402 external beam radiotherapy system
404 magnetic resonance imaging system
406 gantry
408 radiotherapy source
410 collimator
412 magnet
414 cryostat
416 superconducting coil
418 superconducting shield coil
422 bore
424 magnetic field gradient coil
426 magnetic field gradient coil power supply
430 transceiver
432 imaging zone
434 subject support
436 subject
437 mechanical positioning system
438 target zone
440 axis of gantry rotation
442 radiation beam
446 hardware interface
448 processor
450 user interface
452 computer storage
454 computer memory
456 pulse sequences
458 magnetic resonance data
460 magnetic resonance image
462 planning data
464 planning data registration
468 external beam dosage plan
470 cumulative radiation dose
472 control module
474 image reconstruction module
476 image registration module
478 radiotherapy planning module
480 antenna failure model
482 display
484 graphica user interface
486 warning
502 controlling the magnetic resonance imaging system to acquire the magnetic resonance data using the magnetic resonance antenna assembly
504 controlling radiation therapy device to irradiate a target zone within the imaging zone using ionizing radiation
506 measuring the cumulative radiation dose using the multiple electronic dosimeters during irradiation of the target zone
508 predicting a failure of the magnetic resonance antenna assembly using an antenna failure model, the antenna failure model being operable for predicting the failure using the cumulative radiation dose
600 medical instrument
602 subject electronic dosimeters
604 magnet electronic dosimeters
700 medical instrument
702 detector ring
704 control electronics
706 nuclear medical imaging data
708 nuclear medical image
710 concentration of radioisotope
712 emitted radiation

The invention claimed is:

1. A magnetic resonance antenna assembly, comprising:
one or more antenna elements; and
multiple antenna element electronic dosimeters separated and spaced apart from each other and configured to measure a cumulative radiation dose of ionizing radiation received by the magnetic resonance antenna assembly.

2. The magnetic resonance antenna assembly of claim 1, further comprising an antenna element support configured to support the one or more antenna elements, wherein the antenna element dosimeters are distributed within the antenna element support.

3. The magnetic resonance antenna assembly of claim 1, further comprising a radio frequency control component configured to distribute radio-frequency power to the one or more antenna elements, further comprising a set of control component dosimeters, wherein the control component dosimeters are positioned within the radio frequency control component.

4. The magnetic resonance antenna assembly of claim 3, wherein the radio frequency control component is detachable from the magnetic resonance antenna assembly.

5. The magnetic resonance antenna assembly of claim 3, wherein the radio frequency control component is remote from the magnetic resonance antenna assembly.

6. The magnetic resonance antenna assembly of claim 1, wherein the magnetic resonance antenna assembly further comprises a dosimeter controller, wherein the dosimeter controller is configured to electrically power each of the multiple antenna element electronic dosimeters, and wherein the dosimeter controller is configured to determine the cumulative radiation dose of ionizing radiation received by the magnetic resonance antenna assembly using the multiple antenna element electronic dosimeters.

7. The magnetic resonance antenna assembly of claim 6, wherein the dosimeter controller is configured to execute an antenna failure model, wherein the antenna failure model is configured to predict the failure of the magnetic resonance antenna assembly using the cumulative radiation dose.

8. The magnetic resonance antenna assembly of claim 1, further comprising a radio frequency control component configured to receive a radio-frequency signal from the one or more antenna elements, further comprising a set of control component dosimeters, wherein the control component dosimeters are positioned within the radio frequency control component.

9. The magnetic resonance antenna assembly of claim 1, wherein the one or more antenna elements includes a plurality of antenna elements.

10. The magnetic resonance antenna assembly of claim 9, wherein each of at least two of the antenna element electronic dosimeters is disposed within a periphery of a corresponding one of the antenna elements.

11. The magnetic resonance antenna assembly of claim 9, further comprising an antenna element support on which the plurality of antenna elements are supported and on which the multiple antenna element electronic dosimeters are supported.

12. The magnetic resonance antenna assembly of claim 11, wherein each of at least two of the antenna element dosimeters is disposed within a periphery of a corresponding one of the antenna elements.

13. The magnetic resonance antenna assembly of claim 9, further comprising a radio frequency control component configured to receive a radio-frequency signal from the one or more antenna elements, further comprising a plurality of control component dosimeters, wherein the control component dosimeters are positioned within the radio frequency control component.

14. The magnetic resonance antenna assembly of claim 1, wherein the one or more antenna elements comprise a body coil configured for imaging a body of a human subject, further comprising body coil it electronic dosimeters disposed within an interior of the body coil.

15. The magnetic resonance antenna assembly of claim 14, wherein at least one of the body coil electronic dosimeters disposed within an interior of the body coil includes a radiation sensor and electronics for recording the cumulative radiation dose of the ionizing radiation.

16. The magnetic resonance antenna assembly of claim 7, wherein the one or more antenna elements are disposed inside a volume defined by a main magnet, further comprising a plurality of magnet electronic dosimeters attached to the main magnet, wherein the magnet electronic dosimeters are separate from and additional to the antenna element electronic dosimeters and are configured to measure scattered ionized radiation within a main magnetic field which is produced by the main magnet.

17. The magnetic resonance antenna assembly of claim 16, wherein the plurality of magnet electronic dosimeters are connected to the dosimeter controller, wherein the dosimeter controller is further operable for determining a field of radiation dose using the plurality of magnet electronic dosimeters, and wherein the dosimeter controller uses the field of the radiation dose determined from the magnet electronic dosimeters as an additional input for the antenna failure model.

18. A device, comprising:
a plurality of antenna elements;
a plurality of antenna element electronic dosimeters, wherein the antenna element electronic dosimeters are separated and spaced apart from each other and disposed among the plurality of antenna elements; and
a dosimeter controller connected to the plurality of antenna element electronic dosimeters, wherein the dosimeter controller is configured to use outputs of the plurality of antenna element electronic dosimeters to measure a cumulative radiation dose of ionizing radiation received by the magnetic resonance antenna assembly.

19. The device of claim 18, wherein the dosimeter controller is configured to execute an antenna failure model, wherein the antenna failure model is configured to predict the failure of the device using the cumulative radiation dose.

20. A method of operating a medical instrument, wherein the medical instrument comprises a magnetic resonance imaging system operable for acquiring magnetic resonance data from an imaging zone using a magnetic resonance antenna assembly, wherein the magnetic resonance assembly comprises a magnetic resonance antenna assembly, wherein the magnetic resonance antenna assembly comprises one or more antenna elements and a plurality of antenna element electronic dosimeters separated and spaced apart from each other, and wherein the medical instrument further comprises a radiation therapy device, wherein the method comprises:
controlling the magnetic resonance imaging system to acquire the magnetic resonance data using the magnetic resonance antenna assembly;
controlling the radiation therapy device to irradiate a target zone within the imaging zone using ionizing radiation;
during irradiation of the target zone, measuring the cumulative radiation dose for the magnetic resonance antenna assembly from the ionizing radiation using the plurality of antenna element electronic dosimeters which are separated and spaced apart from each other; and
predicting a failure of the magnetic resonance antenna assembly using an antenna failure model, wherein the antenna failure model is operable for predicting the failure using the cumulative radiation dose.

* * * * *